United States Patent
Lee et al.

(10) Patent No.: US 12,392,759 B2
(45) Date of Patent: Aug. 19, 2025

(54) MOVING OBJECT AND CONTROL METHOD FOR THE SAME

(71) Applicants: Hyundai Motor Company, Seoul (KR); Kia Corporation, Seoul (KR)

(72) Inventors: Tae Hee Lee, Yongin-si (KR); Dae Un Sung, Incheon (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 282 days.

(21) Appl. No.: 18/065,037

(22) Filed: Dec. 13, 2022

(65) Prior Publication Data
US 2023/0204557 A1 Jun. 29, 2023

(30) Foreign Application Priority Data
Dec. 28, 2021 (KR) .................. 10-2021-0189298

(51) Int. Cl.
*G01N 33/00* (2006.01)
*G01N 1/22* (2006.01)
*G05D 1/00* (2024.01)

(52) U.S. Cl.
CPC ....... *G01N 33/0073* (2013.01); *G01N 1/2273* (2013.01); *G05D 1/0094* (2013.01); *G05D 1/0212* (2013.01)

(58) Field of Classification Search
CPC ............. G01N 33/0073; G01N 1/2273; G01N 33/0004; G05D 1/0094; G05D 1/0212
See application file for complete search history.

(56) References Cited

U.S. PATENT DOCUMENTS

| | | | |
|---|---|---|---|
| 11,614,430 B2 * | 3/2023 | Buckingham | G01W 1/02 73/23.2 |
| 2012/0151990 A1 * | 6/2012 | Viitala | A61B 5/097 73/23.3 |
| 2014/0023557 A1 | 1/2014 | Tian et al. | |
| 2020/0141734 A1 * | 5/2020 | Casarez | G05B 19/042 |
| 2021/0338028 A1 * | 11/2021 | Park | A47L 9/2894 |
| 2021/0373558 A1 * | 12/2021 | Schneider | G05D 1/0016 |
| 2021/0381934 A1 * | 12/2021 | Abdellatif | B64C 21/02 |
| 2022/0126457 A1 * | 4/2022 | Wu | B25J 9/1674 |
| 2022/0218857 A1 * | 7/2022 | Wu | G05D 1/0248 |
| 2023/0051111 A1 * | 2/2023 | Cyrus | B60K 7/0007 |
| 2023/0213413 A1 * | 7/2023 | Mohr, Jr. | G01N 33/0073 73/31.01 |
| 2023/0249352 A1 * | 8/2023 | Kim | H04N 23/90 |
| 2023/0256371 A1 * | 8/2023 | Seo | G01N 29/024 55/337 |
| 2025/0164338 A1 * | 5/2025 | Rezaei | G05D 1/689 |

FOREIGN PATENT DOCUMENTS

| | | |
|---|---|---|
| JP | 2014021126 A | 2/2014 |
| JP | 5723421 B2 | 5/2015 |
| JP | 6862201 B2 | 4/2021 |
| KR | 20140105262 A | 9/2014 |

\* cited by examiner

*Primary Examiner* — Thomas E Worden
*Assistant Examiner* — Madison B Emmett
(74) *Attorney, Agent, or Firm* — Slater Matsil, LLP

(57) ABSTRACT

An embodiment moving object includes a body, a driving unit, an odor sensing module disposed in the body and including a plurality of gas sensors, and a control unit configured to determine an odor using an output value of each of the gas sensors, determine a movement direction based on a change in concentration of the odor, and control the driving unit to move the body in the determined movement direction.

20 Claims, 12 Drawing Sheets

TARGET PATTERN                    OUTPUT PATTERN

MOVING OBJECT AND CONTROL METHOD FOR THE SAME

CROSS-REFERENCE TO RELATED APPLICATIONS

This application claims the benefit of Korean Patent Application No. 10-2021-0189298, filed on Dec. 28, 2021, which application is hereby incorporated herein by reference.

TECHNICAL FIELD

The present disclosure relates to a moving object and a method for controlling the same.

BACKGROUND

An odor is caused by a mixture of different gases, and recently, odors can be distinguished by using the proportions of components in the mixture of gases or the concentration of an individual gas based on the outputs of a plurality of gas sensors.

Additionally, recently, moving objects such as robots or drones are used to guard facilities or search for missing persons. In general, moving objects can identify objects using image sensors or radar sensors.

Furthermore, the moving objects can autonomously drive based on the objects identified through the image sensors or the radar sensors and perform given tasks while moving through autonomous driving.

SUMMARY

The present disclosure relates to a moving object and a method for controlling the same. Particular embodiments relate to a moving object capable of sensing odor and a method for controlling the same.

There are provided a moving object including an odor sensor module to determine a movement direction based on a change in odor concentration and a method for controlling the same.

A moving object according to an embodiment includes a body, a driving unit configured to move the body, an odor sensing module disposed in the body and including a plurality of gas sensors, and a control unit configured to determine an odor using an output value of each of the plurality of gas sensors, determine a movement direction based on a change in concentration of the odor, and control the driving unit to move the body in the determined movement direction.

The control unit may be configured to control the driving unit to move the body in a direction of increasing concentration of the odor, compare an output pattern of the output values of the plurality of gas sensors with a preset target pattern, control the driving unit to maintain the body in the movement direction when the output pattern and the preset target pattern match, and control the driving unit to turn the body until the output pattern matches the preset target pattern when the output pattern and the preset target pattern do not match.

The control unit may be configured to determine the direction of increasing concentration of the odor by controlling the driving unit to turn the body.

The control unit may be configured to determine the movement direction of the body based on at least one of geographical information or wind direction information when there is no change in the concentration of the odor.

The control unit may be configured to determine a direction in which the output pattern matches the preset target pattern as the body turns and control the driving unit to move the body in the direction of increasing concentration of the odor in the determined direction.

The moving object may further include a communicator.

The control unit may be configured to determine a location at which the concentration of the odor is constantly maintained after the movement of the body in the direction of increasing concentration of the odor and control the communicator to transmit location information of the location to an external device.

The control unit may be configured to control the communicator to transmit information about the direction of increasing concentration of the odor to an external device.

The control unit may be configured to control the driving unit to move the body in the movement direction corresponding to movement direction information when the movement direction information is received through the communicator.

The control unit may be configured to control the driving unit to move the body in a direction of decreasing concentration of the odor.

The control unit may be configured to control the communicator to transmit information about the direction of decreasing concentration of the odor to an external device.

The odor sensing module may further include a needle tube inserted into an odor object to suck a material of the odor object and an actuator to extend or retract the needle tube. The needle tube may include a liquid pipe in which a liquid material included in the material moves and having a drain hole where the liquid material exits, a gas pipe in which a gas material included in the material moves, the gas pipe extended to the plurality of gas sensors, and a separation member to separate the liquid pipe from the gas pipe.

A method for controlling a moving object according to an embodiment, in which the moving object includes a body, a driving unit to move the body, and an odor sensing module disposed in the body and including a plurality of gas sensors, includes determining an odor using an output value of each of the plurality of gas sensors, determining a movement direction based on a change in concentration of the odor, and controlling the driving unit to move the body in the determined movement direction.

Controlling the driving unit to move the body may include controlling the driving unit to move the body in a direction of increasing concentration of the odor, comparing an output pattern of the output values of the plurality of gas sensors with a preset target pattern, controlling the driving unit to maintain the body in the movement direction when the output pattern and the preset target pattern match, and controlling the driving unit to turn the body until the output pattern matches the preset target pattern when the output pattern and the preset target pattern do not match.

The method for controlling a moving object may further include determining the direction of increasing concentration of the odor by controlling the driving unit to turn the body.

The method for controlling a moving object may further include determining the movement direction of the body based on at least one of geographical information or wind direction information when there is no change in the concentration of the odor.

The method for controlling a moving object may further include determining a direction in which the output pattern matches the preset target pattern as the body turns and controlling the driving unit to move the body in the direction of increasing concentration of the odor in the determined direction.

The moving object may further include a communicator.

The method for controlling a moving object may further include determining a location at which the concentration of the odor is constantly maintained after the movement of the body in the direction of increasing concentration of the odor and controlling the communicator to transmit location information of the location to an external device.

The method for controlling a moving object may further include controlling the communicator to transmit information about the direction of increasing concentration of the odor to an external device.

DETAILED DESCRIPTION OF ILLUSTRATIVE EMBODIMENTS

Like reference signs indicate like elements in the specification. The specification does not describe all elements of embodiments, and descriptions generally known in the technical field pertaining to the present disclosure or overlapping descriptions between embodiments are omitted.

In the specification, when an element is referred to as being "connected to" another element, the element may be connected to the other element not only directly but also indirectly, and the indirect connection includes connection via a wireless communication network.

Additionally, unless otherwise stated, the term "comprising" when used in this specification, specifies the presence of stated elements, but does not preclude the presence or addition of one or more other elements.

As used herein, the singular forms include the plural forms as well, unless the context clearly indicates otherwise.

Additionally, the terms " . . . unit", " . . . -er/or", " . . . block", " . . . member" and " . . . module" may refer to a processing unit of at least one function or operation. For example, these terms may refer to at least one hardware of a field-programmable gate array (FPGA)/application specific integrated circuit (ASIC), and at least one process that is processed by at least one software or processor stored in memory.

The reference sign affixed to each step is used to identify each step and these reference signs do not indicate a sequence of steps, and each step may be performed in a different sequence from the disclosed sequence unless a specific sequence is clearly described in the context.

Hereinafter, embodiments of a moving object and a method for controlling the same will be described in detail with reference to the accompanying drawings.

Figure 1:
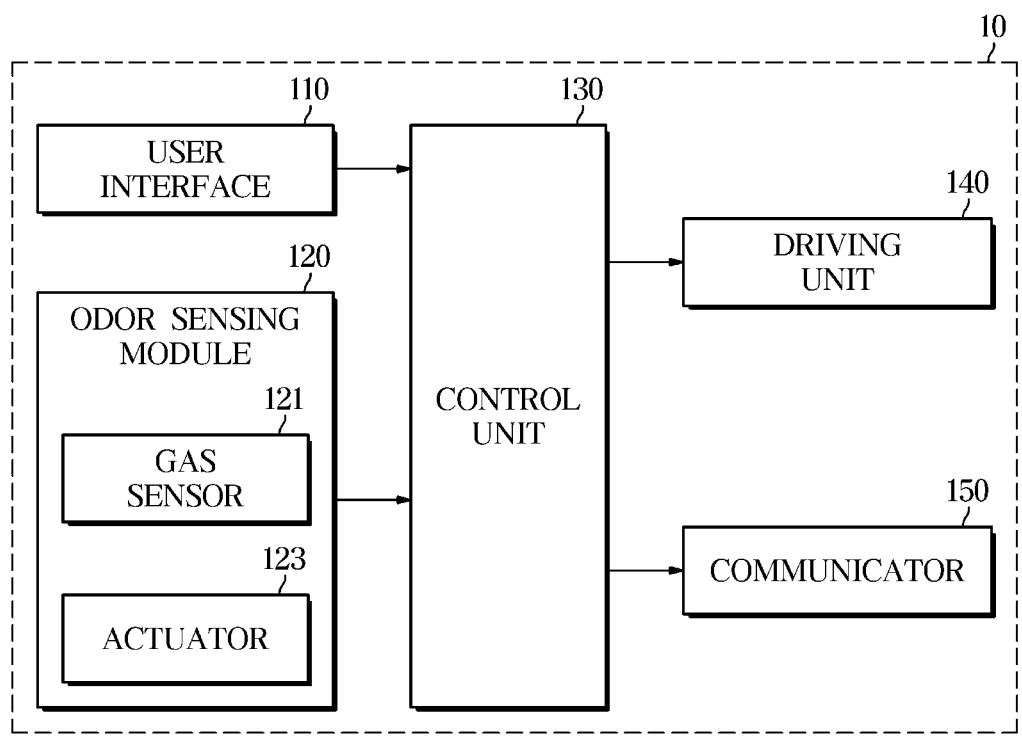
FIG. 1 is a control block diagram of a moving object according to an embodiment.
Figure 2:
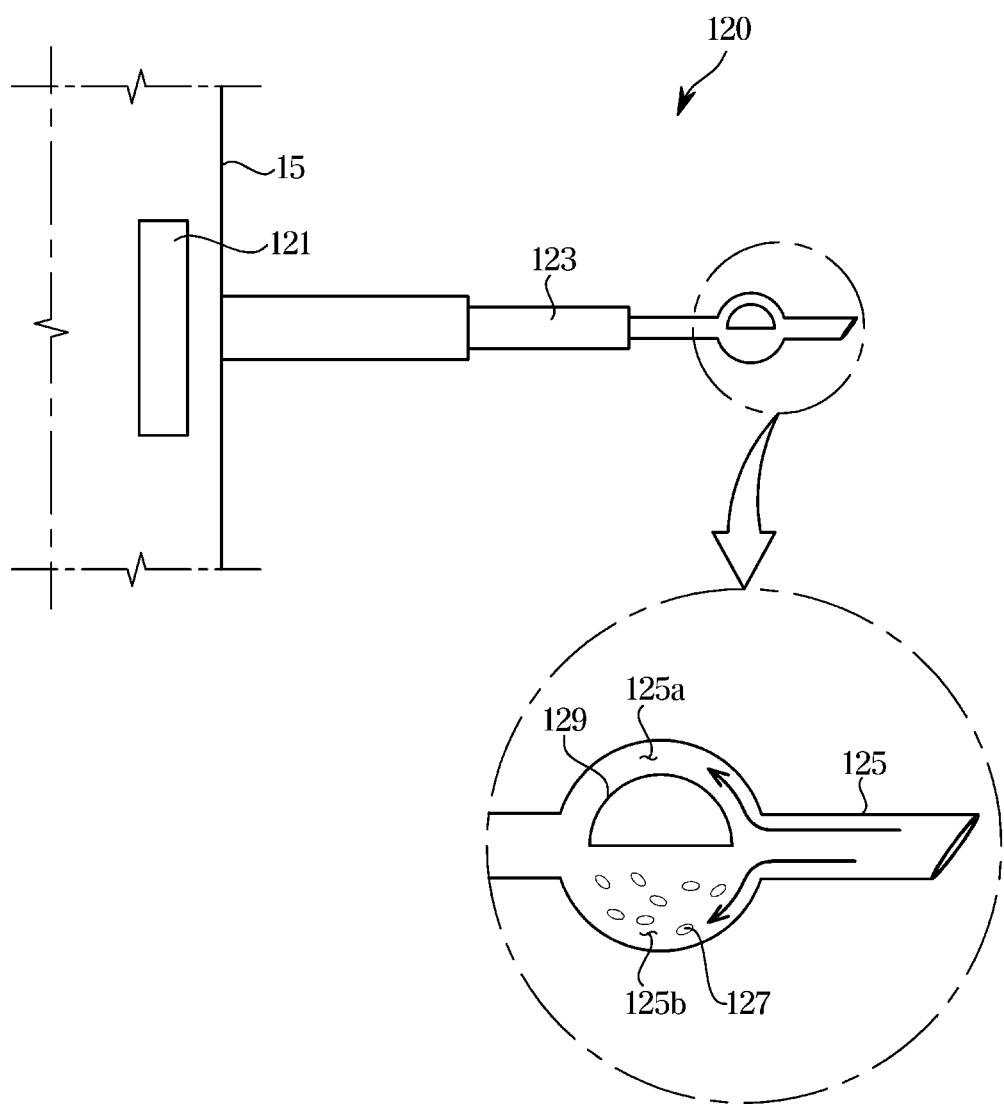
FIG. 2 is a diagram showing the structure of an odor sensing module according to an embodiment.

FIG. 1 is a control block diagram of a moving object according to an embodiment, and FIG. 2 is a diagram showing the structure of an odor sensing module according to an embodiment.

Referring to FIG. 1, a moving object 10 according to an embodiment includes a user interface no to receive a user input or to display information, an odor sensing module 120 to sense an odor, a control unit 130 to control the movement of the moving object 10 based on the sensed odor, a driving unit 140 to move the moving object 10 and a communicator 150 to transmit and receive information to/from an external device.

The moving object 10 is a device that can move based on power and may include a robot, a drone, a vehicle, a personal air vehicle (PAV), and an urban air vehicle (UAM), but its type is not limited thereto.

The user interface 110 according to an embodiment may receive the user input, and to this end, the user interface 110 may include known input devices. For example, the user interface 110 may receive an input target pattern corresponding to a target odor from the user. In this instance, the pattern may refer to a pattern of outputs of a plurality of gas sensors that makes up one odor sensing module 120, and the target pattern may correspond to an output pattern from the odor sensing module 120 for the target odor. That is, the pattern may refer to a relationship between the outputs of the plurality of gas sensors and may be represented by a radar chart, a time-series graph, and a donut graph plotted using the output values of the plurality of gas sensors.

Additionally, the user interface 110 according to an embodiment may display information, and to this end, the user interface 110 may include known display panels.

The odor sensing module 120 according to an embodiment may include the plurality of gas sensors 121, and the plurality of gas sensors 121 may sense the concentration of different types of gases. For example, the plurality of gas sensors 121 may be arranged in an array to measure the concentration of gas flowing in the moving object 10.

The gas sensor 121 may include an electric gas sensor, a chemical gas sensor, or a bio peptide gas sensor, and its type is not limited thereto.

Additionally, as shown in FIG. 2, the odor sensing module 120 may include a needle tube 125 inserted into an odor object to suck a material of the odor object, and an actuator 123 to extend or retract the needle tube 125.

The needle tube 125 may be disposed in a body 15 of the moving object 10 and may be extendable or retractable, and the gas sensors 121 in the body 15 may be disposed at the end of the needle tube 125.

Additionally, the needle tube 125 may include a gas pipe 125a in which a gas material included in the material moves, the gas pipe 125a extended to the plurality of gas sensors, and a liquid pipe 125b in which a liquid material included in the material moves, and having a drain hole 127 through which the liquid material exits, and may include a separation member 129 to separate the gas pipe 125a from the liquid pipe 125b.

Although not shown, the odor sensing module 120 may further include a pump or a suction fan to suck gas and a fan to force out the gas.

The control unit 130 according to an embodiment may determine the odor using the output value of each of the plurality of gas sensors 121.

Specifically, the control unit 130 may identify pattern data corresponding to the output pattern by comparing the output pattern of the output values of the plurality of gas sensors with training pattern data and determine the odor corresponding to the identified pattern data as the odor identified at the current location.

For example, the control unit 130 may train the neural network by supervised learning based on the odor and the outputs of the gas sensors 121 for the odor, and subsequently, the control unit 130 may identify the odor based on the output of the neural network to which the outputs of the gas sensors 121 are input.

The control unit 130 according to an embodiment may determine a movement direction of the moving object 10 based on a change in concentration of the determined odor and control the driving unit 140 to move the body 15 of the moving object 10 in the determined movement direction. The determination of the movement direction and the control of the driving unit 140 by the control unit 130 will be described in more detail below.

The control unit 130 according to an embodiment may control the driving unit 140 to move the body 15 in a direction of increasing odor concentration.

In this instance, the control unit 130 may compare the output pattern of the output values of the plurality of gas sensors 121 with the preset target pattern, and when the output pattern and the preset target pattern match, may control the driving unit 140 to maintain the body 15 in the movement direction, and when the output pattern and the preset target pattern do not match, may control the driving unit 140 to turn the body 15 until the output pattern matches the preset target pattern.

According to an embodiment, the control unit 130 may determine the direction of increasing odor concentration by controlling the driving unit 140 to turn the body 15.

Additionally, according to an embodiment, when there is no change in odor concentration, the control unit 130 may determine the movement direction of the body 15 based on at least one of geographical information or wind direction information. For example, the control unit 130 may determine the movement direction that may face a valley or a drain at which the odor object is expected to be located based on the geographical information. In another example, the control unit 130 may determine the movement direction that may face a direction from which the wind comes based on the wind direction information.

When the body 15 turns due to the mismatch between the output pattern and the preset target pattern, the control unit 130 according to an embodiment may determine a direction in which the output pattern matches the preset target pattern and determine the movement direction based on the odor concentration in the determined direction. That is, the control unit 130 may control the driving unit 140 to move the body 15 in the direction of increasing odor concentration in the corresponding direction.

When a location at which the odor concentration is constantly maintained is determined after the movement of the body 15 in the direction of increasing odor concentration, the control unit 130 according to an embodiment may control the communicator 150 to transmit location information of the location to the external device. That is, when the odor concentration is constantly maintained after the movement in the direction of increasing odor concentration, the control unit 130 may determine the corresponding location as the location of the odor object, and control the communicator 150 to transmit the location information of the corresponding location to the external device (for example, a server or a user terminal) to provide the location of the odor object to the user.

The control unit 130 according to an embodiment may control the communicator 150 to transmit information about the direction of increasing odor concentration to the external device (for example, another moving body or a server). Through this, another moving body also can move to the same destination as the moving object 10, so it is possible to effectively find the odor producing material.

When the movement direction information is received through the communicator 150, the control unit 130 according to an embodiment may control the driving unit 140 to move the body 15 in the movement direction corresponding to the movement direction information.

The control unit 130 according to an embodiment may control the driving unit 140 to move the body 15 in a direction of decreasing odor concentration. In this case, the control unit 130 may control the communicator 150 to transmit information about the direction of decreasing odor concentration to the external device (for example, another moving body or a server).

The control unit 130 may include at least one memory that stores programs for performing the above-described operation and the following operation and at least one processor to run the stored program. When the control unit 130 includes a plurality of memory and a plurality of processors, the plurality of memory and the plurality of processors may be integrated into one chip or may be disposed at physically separated locations.

The driving unit 140 according to an embodiment is a device that supplies the power to move the moving object 10 and can perform steering and braking. The driving unit 140 may include, without limitation, any type of device capable of moving the moving object 10.

The communicator 150 according to an embodiment may transmit and receive information to/from the external device, and to this end, the communicator 150 may include known wireless communication modules.

Hereinabove, components of the moving object 10 has been described. Hereinafter, the movement of the moving object 10 based on the odor concentration will be described.

Figure 3:
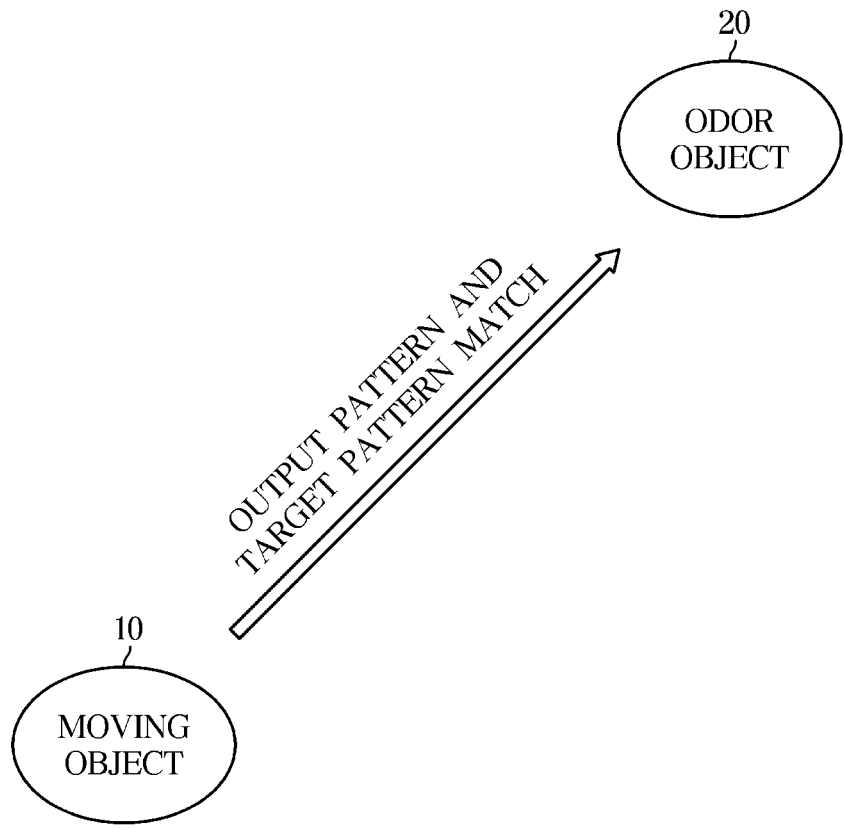
FIG. 3 is a diagram illustrating that a moving object according to an embodiment moves in a direction of increasing odor concentration.
Figure 4:
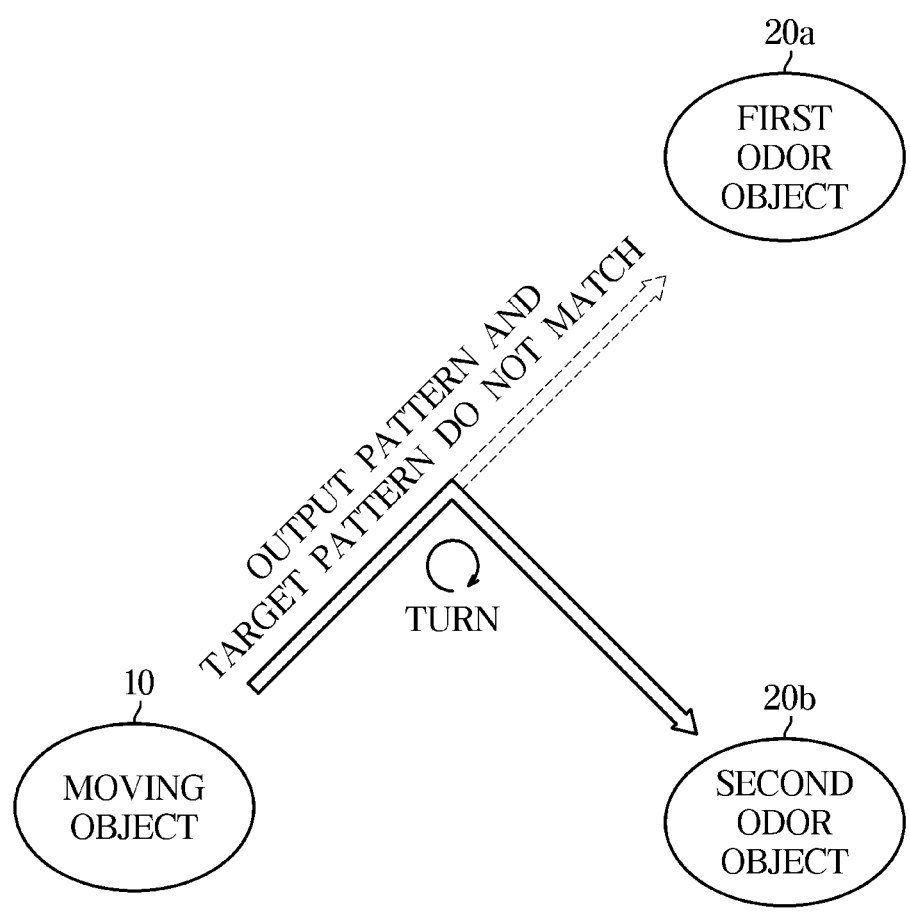
FIG. 4 is a diagram illustrating that an output pattern of an odor sensing module does not match a target pattern while a moving object according to an embodiment is moving in a direction of increasing odor concentration.
Figure 5:
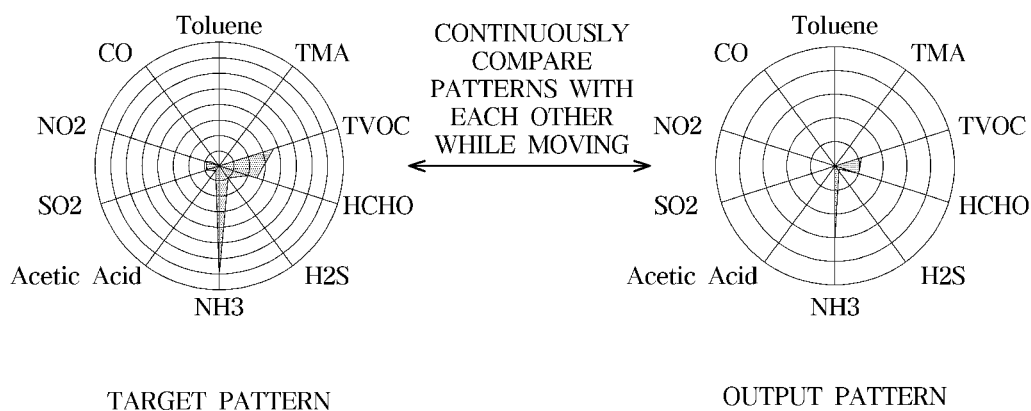
FIG. 5 is a diagram illustrating that a moving object according to an embodiment compares an output pattern with a target pattern.
Figure 6:
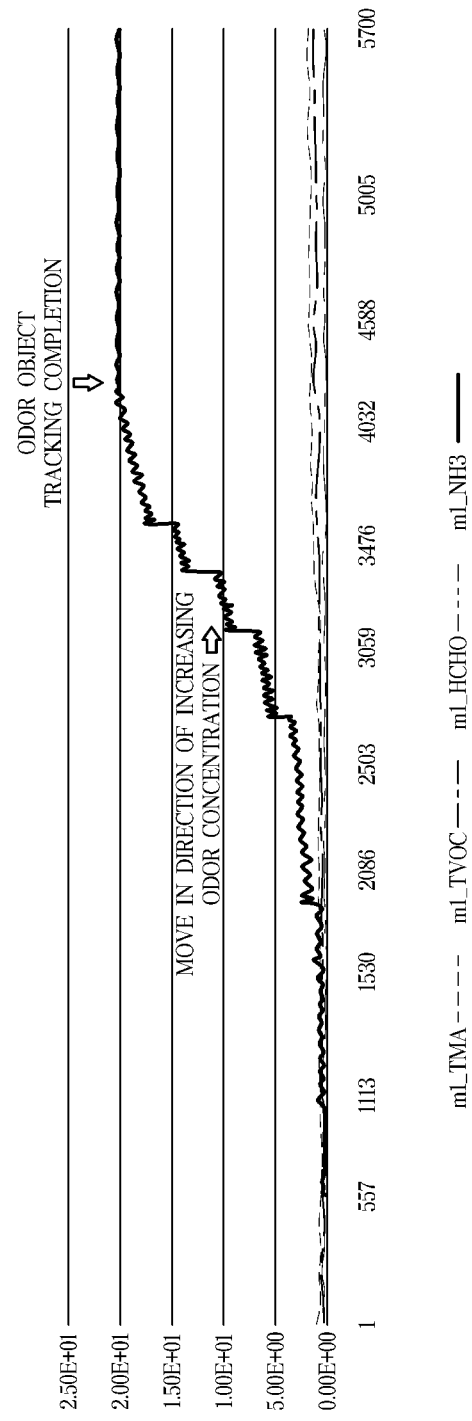
FIG. 6 is a diagram showing the odor concentration when a moving object according to an embodiment moves in a direction of increasing odor concentration.

FIG. 3 is a diagram illustrating that the moving object 10 according to an embodiment moves in the direction of increasing odor concentration, FIG. 4 is a diagram illustrating that the output pattern of the odor sensing module 120 does not match the target pattern while the moving object 10 according to an embodiment is moving in the direction of increasing odor concentration, FIG. 5 is a diagram illustrating that the moving object 10 according to an embodiment compares the output pattern with the target pattern, and FIG. 6 is a diagram showing the odor concentration when the moving object 10 according to an embodiment moves in the direction of increasing odor concentration.

Referring to FIG. 3, the moving object 10 according to an embodiment may move in the direction of increasing odor concentration.

In this instance, the moving object 10 may determine the direction of increasing odor concentration by controlling the driving unit 140 to turn the body 15.

Additionally, according to an embodiment, when there is no change in odor concentration in any direction, the moving object 10 may determine the movement direction of the body 15 based on at least one of environment information such as geographical information or wind direction information. For example, the moving object 10 may determine the movement direction that may face a valley or a drain at which the odor object is expected to be located based on the geographical information. In another example, the moving object 10 may determine the movement direction that may face a direction from which the wind comes based on the wind direction information.

The moving object 10 according to an embodiment may compare the output pattern of the output values of the plurality of gas sensors 121 with the preset target pattern while the moving object 10 is moving in the direction of increasing odor concentration.

As shown in FIG. 5, the pattern may refer to a pattern of outputs of the plurality of gas sensors that makes up one odor sensing module 120, and the target pattern may correspond to an output pattern from the odor sensing module 120 for the target odor. That is, the pattern may refer to a relationship between the outputs of the plurality of gas sensors and may be represented by a radar chart, a time-series graph, and a donut graph plotted using the output values of the plurality of gas sensors. For example, FIG. 5 shows the pattern by representing the output values of the plurality of gas sensors in a radar chart.

Specifically, the moving object 10 may identify pattern data corresponding to the output pattern by comparing the output pattern of the output values of the plurality of gas sensors with training pattern data and determine the odor corresponding to the identified pattern data as the odor identified at the current location.

For example, the moving object 10 may train the neural network by supervised learning based on the odor and the outputs of the gas sensors 121 for the odor, and subsequently, the moving object 10 may identify the odor based on the output of the neural network to which the outputs of the gas sensors 121 are input.

In this instance, as shown in FIG. 3, when the output pattern and the preset target pattern match, the moving object 10 may control the driving unit 140 to maintain the body 15 in the movement direction. As described above, the moving object 10 may move in the direction of increasing odor concentration of the target odor object 20 and reach the odor object 20.

Additionally, as shown in FIG. 4, when the output pattern of the output values of the plurality of gas sensors 121 and the preset target pattern do not match, the moving object 10 may control the driving unit 140 to turn the body 15 until the output pattern matches the preset target pattern. That is, when the odor having the increasing concentration does not have the target pattern while the moving object 10 is moving in the direction of increasing odor concentration, the moving object 10 may turn until the odor of the target pattern is identified, and when the odor for which the output pattern is the target pattern is identified, may move in the corresponding direction. In other words, during the movement of the moving object 10 in the direction of increasing odor concentration of a first odor object 20a, when the corresponding odor is not the target odor, the moving object 10 may turn to find the target odor and move to a second odor object 20b that produces the target odor.

Specifically, when the body 15 turns due to the mismatch between the output pattern and the preset target pattern, the moving object 10 may determine the direction in which the output pattern matches the preset target pattern and determine the movement direction based on the odor concentration in the determined direction. That is, the moving object 10 may control the driving unit 140 to move the body 15 in the direction of increasing odor concentration in the corresponding direction.

As shown in FIG. 6, when the location at which the odor concentration is constantly maintained is determined after the movement of the body 15 in the direction of increasing odor concentration, the moving object 10 according to an embodiment may control the communicator 150 to transmit the location information of the location to the external device. That is, when the odor concentration is constantly maintained after the movement in the direction of increasing odor concentration, the moving object 10 may determine the corresponding location as the location of the odor object and control the communicator 150 to transmit the location information of the corresponding location to the external device (for example, a server or a user terminal) to provide the location of the odor object to the user.

Figure 7:
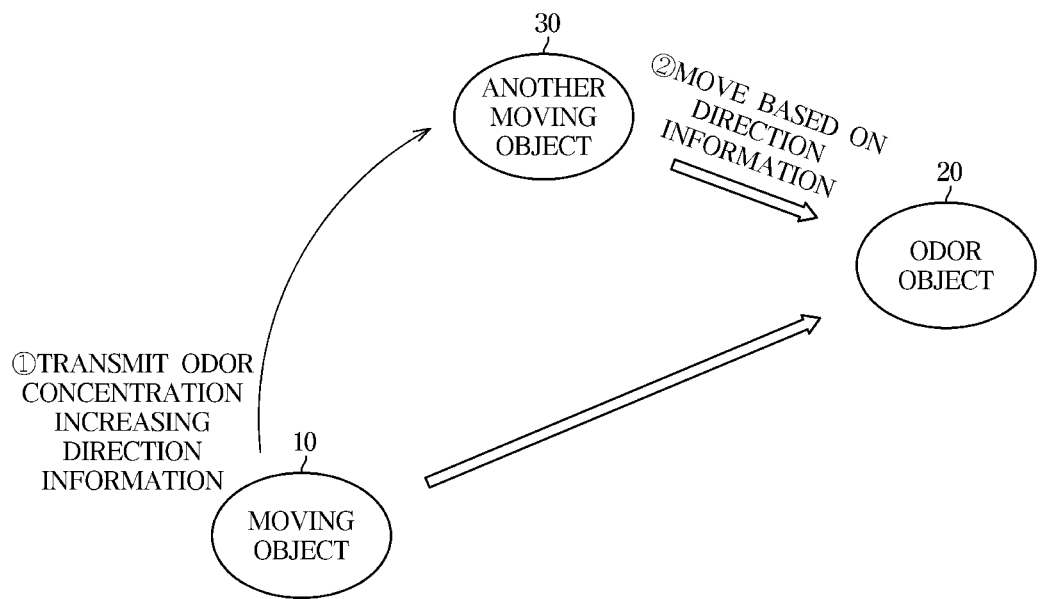
FIG. 7 is a diagram illustrating that a moving object according to an embodiment transmits information about a direction of increasing odor concentration to an external device.
Figure 8:
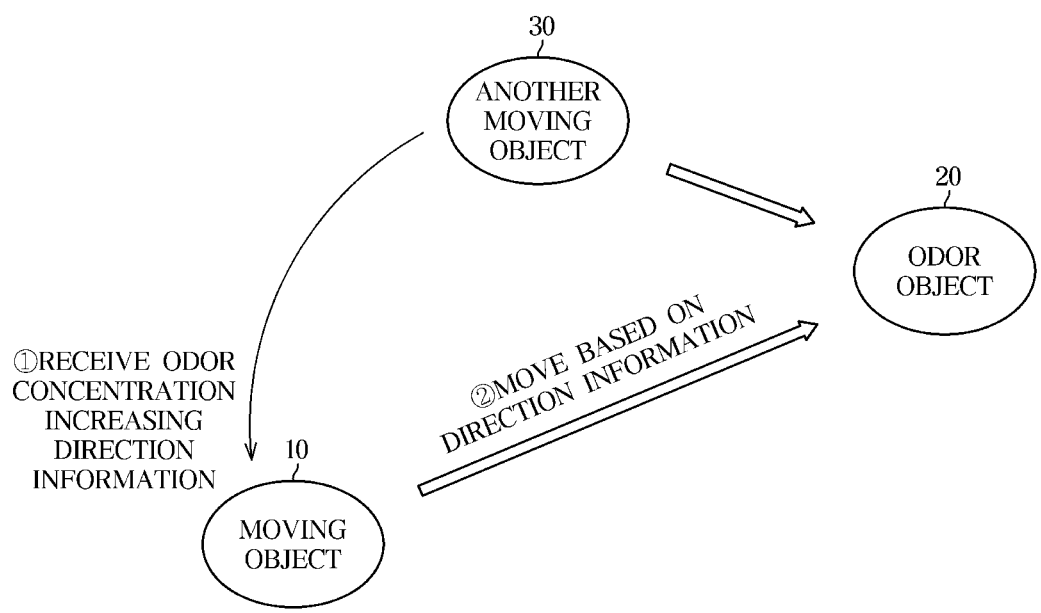
FIG. 8 is a diagram illustrating that a moving object according to an embodiment receives information about a direction of increasing odor concentration from an external device.

FIG. 7 is a diagram illustrating that the moving object 10 according to an embodiment transmits the information about the direction of increasing odor concentration to the external device, and FIG. 8 is a diagram illustrating that the moving object 10 according to an embodiment receives the information about the direction of increasing odor concentration from the external device.

Referring to FIG. 7, the moving object 10 according to an embodiment may control the communicator 150 to transmit the information about the direction of increasing odor concentration to the external device (for example, another moving body 30 or a server). Through this, the other moving body 30 also can move to the same destination as the moving object 10, so it is possible to effectively find the odor object 20.

Additionally, when the movement direction information is received through the communicator 150, the moving object 10 according to an embodiment may control the driving unit 140 to move the body 15 in the movement direction corresponding to the movement direction information. For example, as shown in FIG. 8, when the information about the direction of increasing odor concentration is received from the another moving body 30, the moving object 10 may move to the same destination as the another moving body 30 based on the direction information, so it is possible to effectively find the odor object 20.

Figure 9:
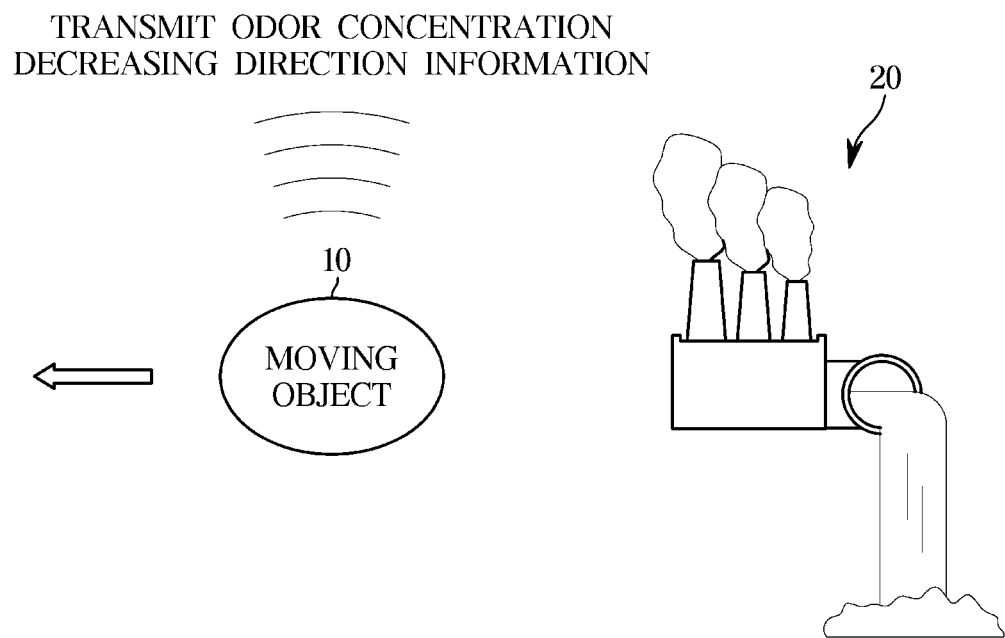
FIG. 9 is a diagram showing that a moving object according to an embodiment moves in a direction of decreasing odor concentration.

FIG. 9 is a diagram showing that the moving object 10 according to an embodiment moves in the direction of decreasing odor concentration.

Referring to FIG. 9, the moving object 10 may control the driving unit 140 to move the body 15 in the direction of decreasing odor concentration. In this case, the moving object 10 may control the communicator 150 to transmit the information about the direction of decreasing odor concentration to the external device (for example, another moving body or a server).

For example, the moving object 10 may correspond to a vehicle that autonomously drives to the destination, and when the odor object 20 that produces offensive odor such as a factory is present on the path, may select a travel path avoiding the odor object 20 and autonomously drive, and may transmit direction information to another moving body or a server to allow another moving body to avoid the odor object 20.

Hereinafter, an embodiment of a method for controlling the moving object 10 will be described. The method for controlling the moving object 10 may use the moving object 10 according to the above-described embodiment. Accordingly, the foregoing description made with reference to FIGS. 1 to 9 may be equally applied to the method for controlling the moving object 10.

Figure 10:
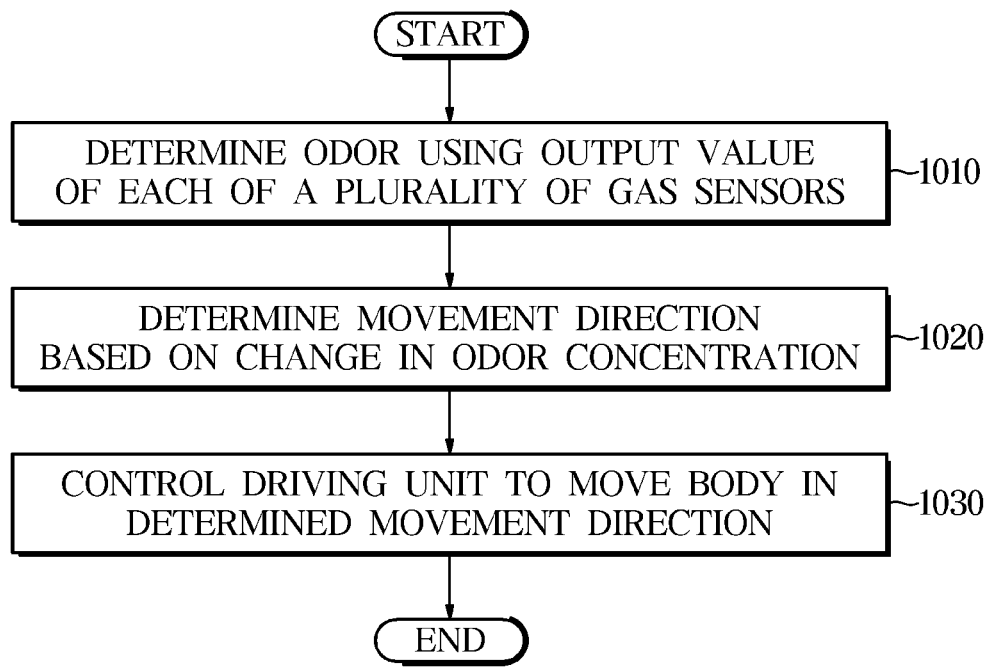
FIG. 10 is a flowchart of the movement of a moving object based on a change in odor concentration in a method for controlling the moving object according to an embodiment.

FIG. 10 is a flowchart of the movement based on the change in odor concentration in the method for controlling the moving object 10 according to an embodiment.

Referring to FIG. 10, the moving object 10 according to an embodiment may determine the odor using the output value of each of the plurality of gas sensors 121 (1010), determine the movement direction based on the change in odor concentration (1020), and control the driving unit 140 to move the body 15 in the determined movement direction (1030).

Figure 11:
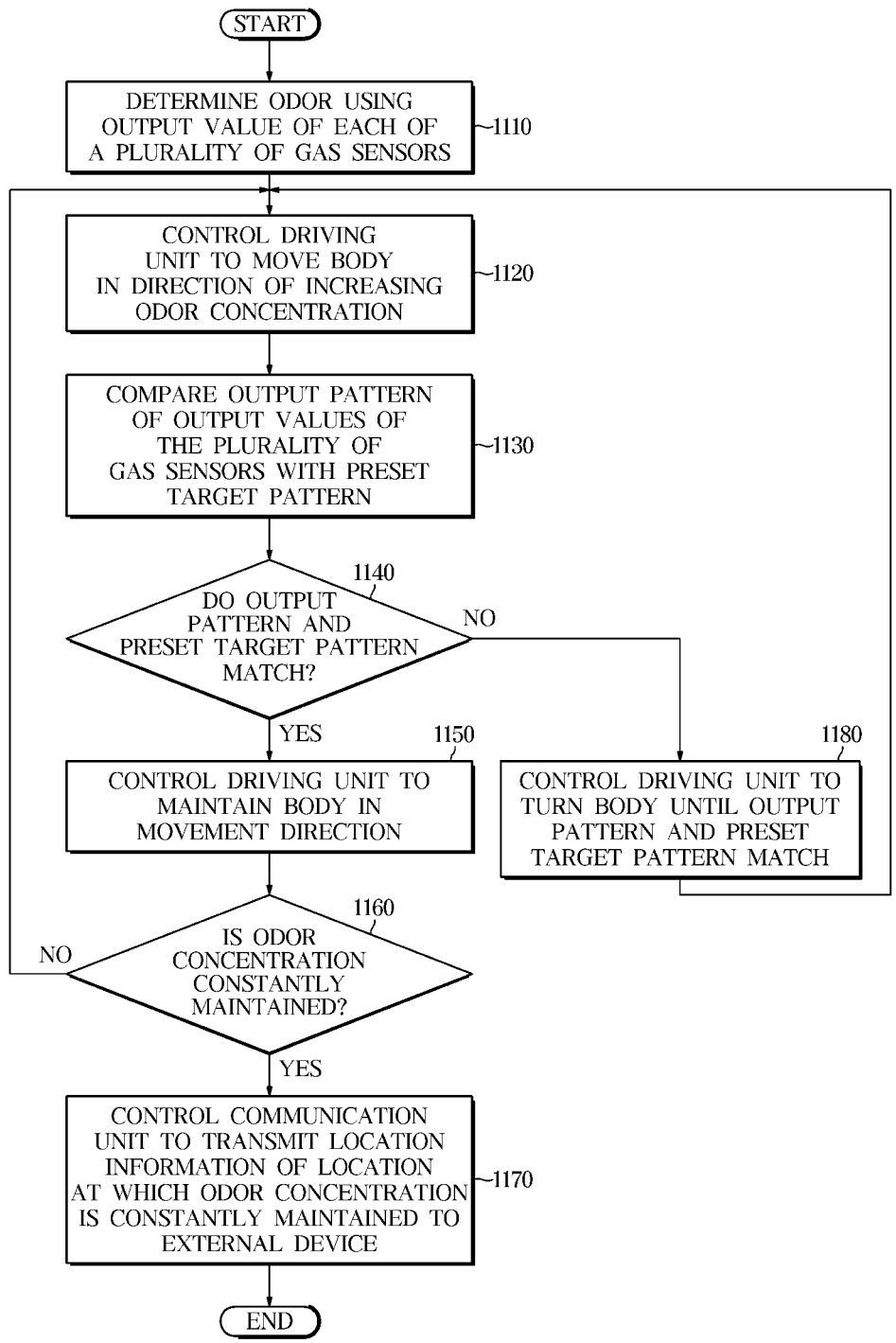
FIG. 11 is a flowchart of the movement of a moving object in a direction of increasing odor concentration in a method for controlling the moving object according to an embodiment.

FIG. 11 is a flowchart of the movement in the direction of increasing odor concentration in the method for controlling the moving object 10 according to an embodiment.

Referring to FIG. 11, the moving object 10 according to an embodiment may determine the odor using the output value of each of the plurality of gas sensors 121 (1110).

Specifically, the control unit 130 may identify pattern data corresponding to the output pattern by comparing the output pattern of the output values of the plurality of gas sensors with training pattern data and determine the odor corresponding to the identified pattern data as the odor identified at the current location.

For example, the control unit 130 may train the neural network by supervised learning based on the odor and the outputs of the gas sensors 121 for the odor, and subsequently, the control unit 130 may identify the odor based on the output of the neural network to which the outputs of the gas sensors 121 are input.

The moving object 10 according to an embodiment may control the driving unit 140 to move the body 15 in the direction of increasing odor concentration (1120).

In this instance, the moving object 10 may determine the direction of increasing odor concentration by controlling the driving unit 140 to turn the body 15.

Additionally, according to embodiments, when there is no change in odor concentration in any direction, the moving object 10 may determine the movement direction of the body 15 based on at least one of environment information such as geographical information or wind direction information.

The moving object 10 according to an embodiment may compare the output pattern of the output values of the plurality of gas sensors 121 with the preset target pattern (1130), and when the output pattern and the preset target pattern match (Yes in 1140), may control the driving unit 140 to maintain the body 15 in the movement direction (1150).

The pattern may refer to a pattern of outputs of the plurality of gas sensors that makes up one odor sensing module 120, and the target pattern may correspond to an output pattern from the odor sensing module 120 for the target odor. That is, the pattern may refer to a relationship between the outputs of the plurality of gas sensors, and may be represented by a radar chart, a time-series graph, and a donut graph plotted using the output values of the plurality of gas sensors.

Specifically, the moving object 10 may identify pattern data corresponding to the output pattern by comparing the output pattern of the output values of the plurality of gas sensors with training pattern data and determine the odor corresponding to the identified pattern data as the odor identified at the current location.

In this instance, when the output pattern and the preset target pattern match, the moving object 10 may control the driving unit 140 to maintain the body 15 in the movement direction. As described above, the moving object 10 may move in the direction of increasing odor concentration of the target odor object 20 and reach the odor object 20.

When the odor concentration is constantly maintained (Yes in 1160), the moving object 10 according to an embodiment may control the communicator 150 to transmit the location information of the location at which the odor concentration is constantly maintained to the external device (1170). When the odor concentration is constantly maintained after the movement of the moving object 10 in the direction of increasing odor concentration, the moving object 10 may determine the corresponding location as the location of the odor object, and control the communicator 150 to transmit the location information of the corresponding location to the external device (for example, a server or a user terminal) to provide the location of the odor object to the user.

When the output pattern and the preset target pattern do not match (No in 1140), the moving object 10 according to an embodiment may control the driving unit 140 to turn the body 15 until the output pattern and the preset target pattern match (1180).

That is, when the odor having the increasing concentration does not have the target pattern while the moving object 10 is moving in the direction of increasing odor concentration, the moving object 10 may turn until the odor of the target pattern is identified, and when the odor for which the output pattern is the target pattern is identified, may move in the corresponding direction.

Figure 12:
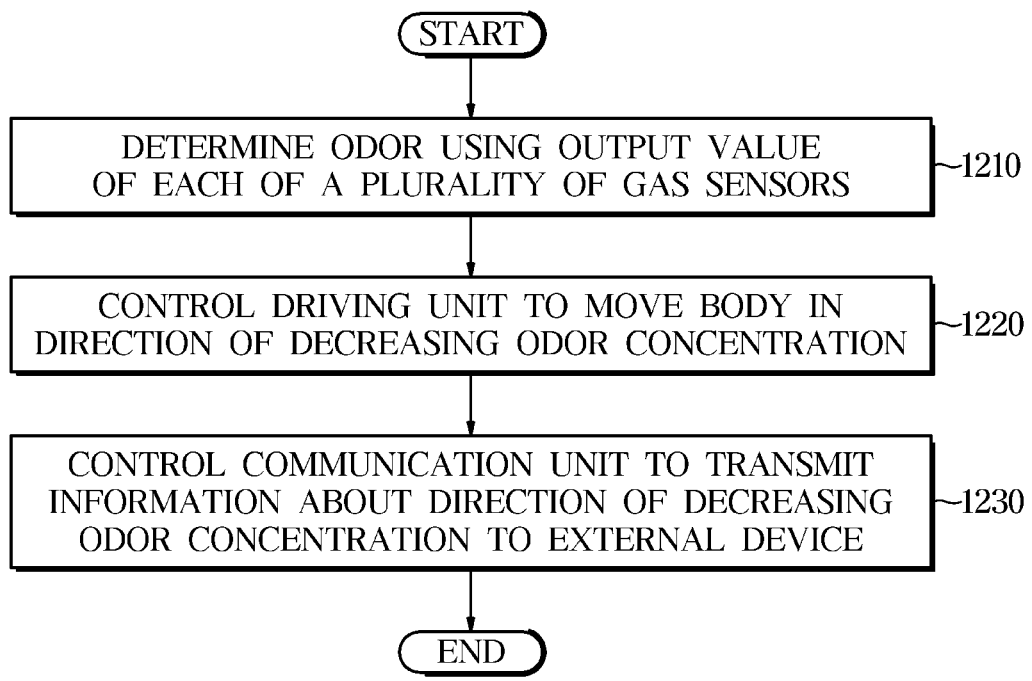
FIG. 12 is a flowchart of the movement of a moving object in a direction of decreasing odor concentration in a method for controlling the moving object according to an embodiment.

FIG. 12 is a flowchart of the movement in the direction of decreasing odor concentration in the method for controlling the moving object 10 according to an embodiment.

Referring to FIG. 12, the moving object 10 according to an embodiment may determine the odor using the output value of each of the plurality of gas sensors 121 (1210), control the driving unit 140 to move the body 15 in the direction of decreasing odor concentration (1220), and control the communicator 150 to transmit the information about the direction of decreasing odor concentration to the external device (1230).

According to the moving object according to an embodiment and the method for controlling the same, the odor sensor module is included to determine a movement direction based on a change in odor concentration, thereby finding or avoiding an odor producing material.

The disclosed embodiments may be implemented in a recording medium that stores computer executable instructions. The instructions may be stored in a program code format, and when executed by a processor, may generate a program module to perform the operations of the disclosed embodiments. The recording medium may be implemented as a computer-readable recording medium.

The computer-readable recording medium includes any type of recording medium in which computer-readable instructions are stored. For example, the computer-readable recording medium may include read only memory (ROM), random access memory (RAM), a magnetic tape, a magnetic disc, a flash memory, and an optical data storage device.

The disclosed embodiments have been hereinabove described with reference to the accompanying drawings. It will be understood by those having ordinary skill in the art pertaining to the present disclosure that the present disclosure may be embodied in different forms from the disclosed embodiments without any change to the technical spirit or essential features of the present disclosure. The disclosed embodiments are provided by way of illustration and should not be interpreted as limiting the present disclosure.

What is claimed is:

1. A moving object comprising:
a body;
a driving unit;
an odor sensing module disposed in the body, the odor sensing module comprising a plurality of gas sensors; and
a control unit configured to determine an odor using an output value of each of the gas sensors, to determine a movement direction based on a change in concentration of the odor, and to control the driving unit to move the body in the determined movement direction, wherein the movement direction of the body is determined based on geographical information in response to determining that there is no change in the concentration of the odor.

2. The moving object according to claim 1, wherein the control unit is configured to:
control the driving unit to move the body in a direction of increasing concentration of the odor;
compare an output pattern of the output value of each of the gas sensors with a preset target pattern;
control the driving unit to maintain the body in the movement direction when the output pattern and the preset target pattern match; and
control the driving unit to turn the body until the output pattern matches the preset target pattern when the output pattern and the preset target pattern do not match.

3. The moving object according to claim 2, wherein the control unit is configured to determine the direction of increasing concentration of the odor by controlling the driving unit to turn the body.

4. The moving object according to claim 2, wherein the control unit is configured to determine a direction in which the output pattern matches the preset target pattern as the body turns and to control the driving unit to move the body in the direction of increasing concentration of the odor in the determined direction.

5. The moving object according to claim 1, wherein the control unit is configured to determine the movement direction of the body based on the geographical information or wind direction information when there is no change in the concentration of the odor.

6. The moving object according to claim 1, wherein the odor sensing module further comprises:
a needle tube inserted into an odor object to suck a material of the odor object, wherein the needle tube comprises:
a liquid pipe in which a liquid material included in the material moves, the liquid pipe comprising a drain hole where the liquid material exits;
a gas pipe in which a gas material included in the material moves, the gas pipe extended to the plurality of gas sensors; and
a separation member separating the liquid pipe from the gas pipe; and
an actuator configured to extend or retract the needle tube.

7. A moving object comprising:
a body;
a driving unit;
a communicator;
an odor sensing module disposed in the body, the odor sensing module comprising a plurality of gas sensors; and
a control unit operatively coupled to the communicator and configured to determine an odor using an output value of each of the gas sensors, to determine a movement direction based on a change in concentration of the odor, and to control the driving unit to move the body in the determined movement direction, wherein the movement direction of the body is determined based on geographical information in response to determining that there is no change in the concentration of the odor.

8. The moving object according to claim 7, wherein the control unit is configured to determine a location at which the concentration of the odor is constantly maintained after the movement of the body in the direction of increasing concentration of the odor and to control the communicator to transmit location information of the location to an external device.

9. The moving object according to claim 7, wherein the control unit is configured to control the communicator to transmit information about the direction of increasing concentration of the odor to an external device.

10. The moving object according to claim 7, wherein the control unit is configured to control the driving unit to move the body in the movement direction corresponding to movement direction information when the movement direction information is received through the communicator.

11. The moving object according to claim 7, wherein the control unit is configured to control the driving unit to move the body in a direction of decreasing concentration of the odor.

12. The moving object according to claim 11, wherein the control unit is configured to control the communicator to transmit information about the direction of decreasing concentration of the odor to an external device.

13. A method for controlling a moving object, the moving object comprising a body, a driving unit, and an odor sensing module disposed in the body and comprising a plurality of gas sensors, the method comprising:
determining an odor using an output value of each of the gas sensors;
determining a movement direction based on a change in concentration of the odor; and
controlling the driving unit to move the body in the determined movement direction, wherein controlling the driving unit to move the body further comprises determining the movement direction of the body based on geographical information in response to determining that there is no change in the concentration of the odor.

14. The method according to claim 13, wherein controlling the driving unit to move the body comprises:
controlling the driving unit to move the body in a direction of increasing concentration of the odor;
comparing an output pattern of the output value of each of the gas sensors with a preset target pattern;
controlling the driving unit to maintain the body in the movement direction when the output pattern and the preset target pattern match; and
controlling the driving unit to turn the body until the output pattern matches the preset target pattern when the output pattern and the preset target pattern do not match.

15. The method according to claim 14, further comprising determining the direction of increasing concentration of the odor by controlling the driving unit to turn the body.

16. The method according to claim 14, further comprising:
determining a direction in which the output pattern matches the preset target pattern as the body turns; and
controlling the driving unit to move the body in the direction of increasing concentration of the odor in the determined direction.

17. The method according to claim 13, further comprising determining the movement direction of the body based on the geographical information or wind direction information when there is no change in the concentration of the odor.

18. The method according to claim 13, wherein the moving object further comprises a communicator.

19. The method according to claim 18, further comprising:
determining a location at which the concentration of the odor is constantly maintained after the movement of the body in the direction of increasing concentration of the odor; and
controlling the communicator to transmit location information of the location to an external device.

20. The method according to claim 18, further comprising controlling the communicator to transmit information about the direction of increasing concentration of the odor to an external device.

* * * * *